US007238357B2

(12) United States Patent
Barron

(10) Patent No.: US 7,238,357 B2
(45) Date of Patent: Jul. 3, 2007

(54) METHODS FOR TREATING ULCERS AND GASTROESOPHAGEAL REFLUX DISEASE

(75) Inventor: Richard L. Barron, Trabuco Canyon, CA (US)

(73) Assignee: Allergan, Inc., Irvine, CA (US)

( * ) Notice: Subject to any disclaimer, the term of this patent is extended or adjusted under 35 U.S.C. 154(b) by 310 days.

(21) Appl. No.: 10/288,734

(22) Filed: Nov. 5, 2002

(65) Prior Publication Data

US 2004/0086531 A1   May 6, 2004

(51) Int. Cl.
  *A61K 39/08*   (2006.01)
  *A61K 38/16*   (2006.01)
(52) U.S. Cl. .................. 424/239.1; 424/9.1; 424/236.1; 514/2; 514/12; 530/350; 530/412
(58) Field of Classification Search ............. 424/239.1, 424/9.1, 236.1; 514/12, 2; 530/350, 412
See application file for complete search history.

(56) References Cited

U.S. PATENT DOCUMENTS

| | | | | |
|---|---|---|---|---|
| 4,959,384 A | * | 9/1990 | Kraft et al. .................. 514/390 |
| 5,397,770 A | * | 3/1995 | Levin et al. .................... 514/2 |
| 5,437,291 A | | 8/1995 | Pasricha et al. |
| 5,571,116 A | * | 11/1996 | Bolanos et al. ............. 606/139 |
| 5,670,484 A | | 9/1997 | Binder |
| 5,674,205 A | | 10/1997 | Pasricha et al. |
| 5,714,468 A | | 2/1998 | Binder |
| 5,766,605 A | * | 6/1998 | Sanders et al. .......... 424/239.1 |
| 5,989,545 A | | 11/1999 | Foster et al. |
| 6,063,768 A | | 5/2000 | First |
| 6,113,915 A | | 9/2000 | Aoki et al. |
| 6,139,845 A | | 10/2000 | Donovan |
| 6,143,306 A | | 11/2000 | Donovan |
| 6,265,379 B1 | | 7/2001 | Donovan |
| 6,306,403 B1 | | 10/2001 | Donovan |
| 6,306,423 B1 | | 10/2001 | Donovan et al. |
| 6,312,708 B1 | | 11/2001 | Donovan |
| 6,328,977 B1 | | 12/2001 | Donovan |
| 6,358,513 B1 | | 3/2002 | Voet et al. |
| 6,365,164 B1 | | 4/2002 | Schmidt |
| 6,395,277 B1 | | 5/2002 | Graham |
| 6,405,732 B1 | * | 6/2002 | Edwards et al. ............ 128/898 |
| 6,423,319 B1 | | 7/2002 | Brooks et al. |
| 6,458,365 B1 | | 10/2002 | Aoki et al. |
| 6,464,986 B1 | | 10/2002 | Aoki et al. |
| 6,521,255 B2 | * | 2/2003 | Vergez et al. ................ 424/473 |

FOREIGN PATENT DOCUMENTS

| | | |
|---|---|---|
| EP | 0 605 501 B1 | 4/1999 |
| EP | 1 334 729 A1 | 8/2003 |
| WO | WO 94/00481 | 1/1994 |
| WO | WO 95/17904 | 7/1995 |
| WO | WO 01/58472 A2 | 8/2001 |

OTHER PUBLICATIONS

Ravich, William J., *Botulinum toxin for UES dysfunction: Therapy or poison?*, Dysphagia, vol. 16, No. 3, Jul. 2001, pp. 168-170.
Rohrbach, S., et al., *Minimally invasive application of botulinum toxin type A in nasal hypersecretion*, J. Oto-rhino-Laryngol 2001, Nov.-Dec.;63(6):382-4.
Olthoff, A., et al., *Botulinum Toxin type a induces apoptosis in nasal glands of guinea pigs*, J. Oto-rhino-Laryngol 2001 Nov.; 110(11):1045-50.
Sanchez-Prieto, J., *Botulinum toxin A blocks glutamate exocytosis from guinea-pig cerebral cortical synaptosomes*, Eur J Biochem 1987 Jun.;165(3):675-81.
Schantz, E.J., et al., *Preparation and characterization of botulinum toxin type A for human treatment*, Chap 3, pp. 41-49, Therapy with Botulinum Toxin, 1994, Ed. J. Jankovic, et al., Marcel Dekker, Inc. publisher.
Schantz, E.J., et al., *Properties and use of botulinum toxin and other microbial neurotoxins in medicine*, Microbiol Rev 1992 Mar.; 56(1):80-99.
Sloop, R.R., et al., *Reconstituted botulinum toxin type A does not lose potency in humans if it is refrozen or refrigerated for 2 weeks before use*, Neurology 1997 Jan.;48(1):249-53.
Wang, Z, et al., *Effects of botulinum toxin on gastric myoelectrical and vagal activities in dogs*, Gastroenterology 2001 Apr.; 120 (5 Suppl 1):A-718.
Wiegand, H., et al., *I-Labelled botulinum A neurotoxin pharmacokinetics in cats after intramuscular injection*. Naunyn Schmiedebergs Arch Pharmacol, 1976;292:161-5.
Wiesel, P.H., et al., *Botulinum toxin for refractory postoperative pyloric spasm*, Endoscopy 1997;29(2):132.
Spierings, ELH, *Reflux-triggered migraine headache originating from the upper gum/teeth*, Cephalalgia, 2002, 22, pp. 555-556.
Thumshirn, M., *Gastrointestinal motility disorders relevant to general practice*, Schweiz Rundsch Med Prax, Oct. 16, 2002, 91(42), pp. 1741-1747 (abstract, translation from German).
Lew, M.F., *Analysis of the duration of efficacy of botulinum toxin type B in patients with cervical dystonia*, Mov Disord, Sep. 2002, 17(5), p. 1142.
Albanese, A., et al., *The use of botulinum toxin on smooth muscles*, Eur. J. Neurol 1995, Nov.; 2(supp 3): 29-33.
Bigalke, H., et al., *Tetanus toxin and botulinum A toxin inhibit release and uptake of various transmitters, as studied with particulate preparations from rat brain and spinal cord*, Naunyn Schmiedebergs Arch Pharmacol. 1981; 316:244-51.
Bigalke, H., et al., *Botulinum A Neurotoxin inhibits non-cholinergic synaptic transmission in mouse spinal cord neurons in culture*, Brain Res 1985;360: 318-324.
Binz, T., et al., *The complete sequence of botulinum neurotoxin type A and comparison with other clostridial neurotoxins*, y and Molecular Biology, Inc., vol. 265, No. 16, Jun. 5, 1990, pp. 9153-9158.
Boyd, R.S., et al., *The insulin secreting β-cell line, HIT-15, contains SNAP-25 which is a target for botulinum neurotoxin-A*, Mov Disord May 1995; 10(3):376.
Boyd, R.S., et al., *The effect of botulinum neurotoxin-B on insulin release from a β-cell line*, Mov Disord May 1995;10(3):376.

(Continued)

*Primary Examiner*—Chih-Min Kam
(74) *Attorney, Agent, or Firm*—Claude L. Nassif; Stephen Donovan; Martin A. Voet

(57) ABSTRACT

Methods for treating peptic ulcers and methods for treating gastroesophageal reflux disease by oral administration of a botulinum toxin.

12 Claims, 1 Drawing Sheet

OTHER PUBLICATIONS

Coffield, J.A., et al., p. 5, *The site and mechanism of action of botulinum neurotoxin*, Therapy with Botulinum Toxin, 1994, Ed. J. Jankovic, et al., Marcel Dekker, Inc. publisher.

Crowell, M.D., et al., *Botulinum Toxin reduces pyloric dysfunction in patients with diabetic gastroparesis*, Gastroenterology 2002, Apr.; 122(4 Supp 1): A451-A452 (1 page).

Dabrowski, E., et al., *Botulinum toxin as a novel treatment for self mutilation in Lesch-Nyhan Syndrome*, Ann Neurol 2002 Sep.;52(3 Supp 1): S157 ABS 169.

Difazio, M., et al., *A focused review of the use of botulinum toxins for low back pain*, Clin J Pain 2002;18(6 Suppl):S155-S162.

Dykstra, D., et al., *Treatment of detrusor-sphincter dyssynergia with botulinum A toxin: a double blind study*, Arch Phys Med Rehabil 1990 Jan.;71:24-26.

Eaker, E. Y, et al., *Untoward effects of esophageal botulinum toxin injection in the treatment of achalasia*, Dig Dis Sci 1997 Apr.: 42(4):724-7.

Gui, D., et al., *Botulinum toxin injected in the gastric wall reduces body weight and food intake in rats*, Aliment Pharmacol Ther 2000, Jun.:14(6):829-834.

Gui, D. et al., *Effects of botulinum toxin on gastric emptying and digestive secretions. A possible tool for correction of obesity*, Naunyn Schmiedebergs Arch Pharmacol 2002 Jun.:365(Suppl 2):R22.

Habermann, E., et al., *Journal of Neurochemistry*, 51,522-527, 1988.

Habermann, E., *I-labeled Neurotoxin from clostridium botulinum A: preparation, binding to synaptosomes and ascent to the spinal cord*, Naunyn Schmiedebergs Arch Pharmacol 1974; 281:47-56.

Hanson, M.A., et al., *Structural view of botulinum neurotoxin in numerous functional states*, Scientific and therapeutic aspects of botulinum toxin, 2002, ed. M. Brin, et al., Pub.—Lippincott Williams & Wilkins, p. 11-27.

Harrison's principles of internal medicine, 14th Edition, ed. by Fauci, et al., (1998), Table of Contents.

Hoogerwerf, W., et al., *Botulinum toxin for spastic gastrointestinal disorders*, Bailliere's Clin Gastroentero 1999;13(1):131-143.

Kohl, A., et al., *Comparison of the effect of botulinum toxin A (Botox®) with the high-purified neurotoxin (NT 201) in the extensor digitorum brevis muscle test*, MovDisord 2000;15(Suppl 3):165.

Kondo, T., et al., *Modification of the action of pentagastrin on acid secretion by botulinum toxin*, Experientia 1977;33:750- 1.

Laskawi, R., et al., *Up-to-date report of botulinum toxin type A treatment in patients with gustatory sweating (Frey's Syndrome)*, Laryngoscope 1998 Mar.;108(3):381-4.

Marjama-Lyoas, J., et al., *Tremor-predominant Parkinson's disease*, Drugs & Aging 2000 Apr.; 16(4):273-278.

Marchese-Ragona, R., et al., *Management of parotid siatocele with botulinum toxin*, Laryngoscope 1999 Aug.;109(8):1344-1346.

Meyer, K.E., *A comparative systemic toxicity study of neurobloc in adult and juvenile cynomolgus monkeys*, Mov Disord 2000;15(Suppl 2):54.

Naumann, M., et al., *Botulinum toxin type A in the treatment of focal, axillary and palmar hyperhidrosis and other hyperhidrotic conditions*, Euro. J. Neurology, 1999, 6 suppl 4:S111-S115.

Pearce, L. B., et al., *Pharmacologic characterization of botulinum toxin for basic science and medicine*, Toxicon 1997;35(9):1373-412.

Rossi, S., et al., *Immunohistochemical localization of SNAP-25 protein in the stomach of rat*, Naunyn Schmiedebergs Arch Pharmacol, 2002;365(Suppl 2):R37.

\* cited by examiner

METHODS FOR TREATING ULCERS AND GASTROESOPHAGEAL REFLUX DISEASE

BACKGROUND

The present invention relates to methods for treating ulcers and/or for treating gastroesophageal reflux disease. In particular, the present invention relates to methods for treating peptic ulcers and for treating gastroesophageal reflux disease with a botulinum toxin.

Ulcers

During normal digestion, food moves from the mouth down the esophagus into the stomach. The stomach produces hydrochloric acid and the enzyme pepsin to digest the food. From the stomach, food passes into the upper part of the small intestine, the duodenum, where digestion and nutrient absorption continue.

An ulcer is a sore or lesion that forms in the lining of the stomach or duodenum where acid and pepsin are present. Ulcers in the stomach are called gastric or stomach ulcers. Ulcers in the duodenum are called duodenal ulcers. Collectively, ulcers in the stomach and duodenum are called peptic ulcers. Ulcers rarely occur in the esophagus or in the first portion of the duodenum, the duodenal bulb.

About 20 million Americans develop at least one ulcer during their lifetime. Additionally, ulcers affect about 4 million people and more than 40,000 people have surgery each year because of persistent symptoms or problems from ulcers and tragically, about 6,000 people die each year from ulcers or ulcer related complications.

Ulcers can develop at any age, but they are rare among teenagers and even more uncommon in children. Duodenal ulcers occur for the first time usually between the ages of 30 and 50. Stomach ulcers are more likely to develop in people over age 60. Duodenal ulcers occur more frequently in men than women, while stomach ulcers develop more often in women than men.

It is believed that three factors, lifestyle, acid and pepsin, and the bacterium *Helicobacter pylori* play a role in ulcer development. Thus, lifestyle factors such as stress and diet can contribute to ulcer formations. Additionally, an imbalance between digestive fluids (hydrochloric acid and pepsin) and the stomach's ability to defend itself against these powerful substances can result in ulcers. Finally, an ulcer can develop as a result of infection with the *H. pylori.*

The stomach's inability to defend itself against the powerful digestive fluids, acid and pepsin, contributes to ulcer formation. Thus, excessive digestive fluids, acid and/or pepsin present in the stomach, or normal amount of these substances in a compromised stomach can be causative factors in ulcer formation. The stomach defends itself from these fluids in several ways. One way is by producing mucus, a lubricant-like coating which shields stomach tissues. Another way is by producing bicarbonate which neutralizes and breaks down digestive fluids into substances less harmful to stomach tissue. Finally, blood circulation to the stomach lining, cell renewal, and cell repair also help protect the stomach.

*H. Pylori* is a spiral-shaped bacterium found in the stomach. It has been shown that this bacterium (along with acid secretions) can damage stomach and duodenal tissue, causing inflammation and ulcers.

*H. pylori* survives in the stomach because it produces the enzyme urease. Urease generates substances that neutralize the stomach's acid, thereby enabling the bacterium to survive. Because of it's shape and the way it moves, *H. pylori* can penetrate the stomach's protective mucous lining. Here, it can produce substances that weaken the stomach's protective mucus and make the stomach cells more susceptible to the damaging effects of acid and pepsin.

The bacterium can also attach to stomach cells further weakening the stomach's defensive mechanisms and producing local inflammation. For reasons not completely understood, *H. pylori* can also stimulate the stomach to produce more acid.

Excess stomach acid and other irritating factors can cause inflammation of the upper end of the duodenum, the duodenal bulb. In some people, over long periods of time, this inflammation results in production of stomach-like cells called duodenal gastric metaplasia. *H. pylori* then attacks these cells causing further tissue damage and inflammation, which may result in an ulcer.

Within weeks of infection with *H. pylori*, most people develop gastritis, an inflammation of the stomach lining. However, most people will never have symptoms or problems related to the infection. It is not known what is different in those people who develop *H. pylori*-related symptoms or ulcers. Hereditary or environmental factors may cause some individuals to develop problems. Alternatively, symptoms and ulcers may result from infection with more virulent strains of bacteria.

The most common ulcer symptom is a gnawing or burning pain in the abdomen between the breastbone and the navel. The pain often occurs between meals and in the early hours of the morning. It may last from a few minutes to a few hours and may be relieved by eating or by taking antacids.

Less common ulcer symptoms include nausea, vomiting, and loss of appetite and weight. Bleeding from ulcers may occur in the stomach and duodenum. Sometimes patients are unaware that they have a bleeding ulcer, because blood loss is slow and blood may not be obvious in the stool. Such patients can feel tired and weak. If the bleeding is heavy, blood will appear in vomit or stool. Stool containing blood appears tarry or black.

Ulcers can be diagnosed by performing endoscopic and x-ray examinations, and well as by for testing for *H. pylori*. An upper GI series can be used to diagnose ulcers. An upper GI series involves taking an x-ray of the esophagus, stomach, and duodenum to locate an ulcer. To make the ulcer visible on the x-ray image, the patient swallows a chalky liquid called barium.

An alternative diagnostic test is endoscopy during which the patient is lightly sedated and the doctor inserts a small flexible instrument with a camera on the end through the mouth into the esophagus, stomach, and duodenum. With this procedure, the entire upper GI tract can be viewed. Ulcers or other conditions can be diagnosed and photographed, and tissue can be taken for biopsy, if necessary.

Stomach and duodenal ulcers can be treated with H2-blockers, acid (proton) pump inhibitors, and mucosal protective agents. When treating *H. pylori*, these medications are used in combination with antibiotics.

H2-blockers reduce the amount of acid the stomach produces by blocking histamine, a powerful stimulant of acid secretion. Unfortunately, H2-blockers require several weeks to significantly reduce ulcer pain. Furthermore, treatment with H2-blockers lasts 6 to 8 weeks. Nizatidine (Axid®) is approved for treatment of duodenal ulcers but is not yet approved for treatment of stomach ulcers. H2-blockers that are approved to treat both stomach and duodenal ulcers are include Cimetidine (Tagamet®), Ranitidine (Zantac®) and Famotidine (Pepcid®).

Like H2-blockers, acid (proton) pump inhibitors modify the stomach's production of acid. However, acid pump inhibitors more completely block stomach acid production by stopping the stomach's acid pump, the final step of acid secretion. The FDA has approved use of omeprazole for short-term treatment of ulcer disease.

Mucosal protective medications protect the stomach's mucous lining from acid. Unlike H2-blockers and acid pump inhibitors, protective agents do not inhibit the release of acid. These medications shield the stomach's mucous lining from the damage of acid. Two commonly prescribed protective agents are:

Sucralfate (Carafate®). This medication adheres to the ulcer, providing a protective barrier that allows the ulcer to heal and inhibits further damage by stomach acid. Sucralfate is approved for short-term treatment of duodenal ulcers and for maintenance treatment.

Misoprostol (Cytotec®). This synthetic prostaglandin, a substance naturally produced by the body, protects the stomach lining by increasing mucus and bicarbonate production and by enhancing blood flow to the stomach. It is approved only for the prevention of NSAID-induced ulcers.

Two common non-prescription protective medications are: Antacids. Antacids can offer temporary relief from ulcer pain by neutralizing stomach acid. They may also have a mucosal protective role. Many brands of antacids are available without prescription. Bismuth Subsalicylate. Bismuth subsalicylate has both a protective effect and an antibacterial effect against *H. pylori.*

The discovery of the link between ulcers and *H. pylori* has resulted in a new treatment option. Now, in addition to treatment aimed at decreasing the production of stomach acid, doctors may prescribe antibiotics for patients with *H. pylori.* This treatment is a dramatic medical advance because eliminating *H. pylori* means the ulcer may now heal and most likely will not come back.

Various treatment regimes can be used, lasting from two to eight weeks. Thus use of a two week, triple therapy is known. This regimen can eradicate much of the *H. pylori* bacteria and can reduce the risk of recurrence of a duodenal ulcers. Patients with stomach ulcers that are not associated with NSAIDs can also benefit from bacterial eradication. While triple therapy is effective, it is sometimes difficult to follow because the patient must take three different medications four times each day for 2 weeks.

In addition, the treatment commonly causes side effects such as yeast infection in women, stomach upset, nausea, vomiting, bad taste, loose or dark bowel movements, and dizziness. The 2-week, triple therapy combines two antibiotics, tetracycline (e.g., Achromycin® or Sumycin®) and metronidazole (e.g., Flagyl®) with bismuth subsalicylate (Pepto-Bismol®). Some doctors may add an acid-suppressing drug to relieve ulcer pain and promote ulcer healing. In some cases, doctors may substitute amoxicillin (e.g., Amoxil® or Trimox®) for tetracycline or if they expect bacterial resistance to metronidazole, other antibiotics such as clarithromycin (Biaxin®).

As an alternative to triple therapy, two-week, dual therapies are also known. Dual therapy is simpler for patients to follow and causes fewer side effects. A dual therapy might include an antibiotic, such as amoxicillin or clarithromycin, with omeprazole, a drug that stops the production of acid. Unfortunately, it can require from four to eight weeks (i.e. using bismuth, metronidazole, tetracylime) or even longer (i.e. using H2 or proton pump inhibitor) to effectively treat a peptic ulcer with current therapies.

In most cases, anti-ulcer medicines heal ulcers quickly and effectively. Eradication of *H. pylori* prevents most ulcers from recurring. However, patients who do not respond to medication or who develop complications may require surgery. While surgery is usually successful in healing ulcers and preventing their recurrence and future complications, problems can sometimes result.

At present, standard open surgery is performed to treat ulcers. In the future, surgeons may use laparoscopic methods. A laparoscope is a long tube-like instrument with a camera that allows the surgeon to operate through small incisions while watching a video monitor. The common types of surgery for ulcers are vagotomy, pyloroplasty, and antrectomy.

A vagotomy involves cutting the vagus nerve, a nerve that transmits messages from the brain to the stomach. Interrupting the messages sent through the vagus nerve reduces acid secretion. However, the surgery may also interfere with stomach emptying. The newest variation of the surgery involves cutting only parts of the nerve that control the acid-secreting cells of the stomach, thereby avoiding the parts that influence stomach emptying.

In an antrectomy the lower part of the stomach (antrum), which produces a hormone that stimulates the stomach to secrete digestive juices is removed. Sometimes a surgeon may also remove an adjacent part of the stomach that secretes pepsin and acid. A vagotomy is usually done in conjunction with an antrectomy.

Pyloroplasty is another surgical procedure that may be performed along with a vagotomy. Pyloroplasty enlarges the opening into the duodenum and small intestine (pylorus), enabling contents to pass more freely from the stomach.

The complications of ulcers can include bleeding, perforation of the organ walls, and narrowing and obstruction of digestive tract passages. As an ulcer eats into the muscles of the stomach or duodenal wall, blood vessels may also be damaged, which causes bleeding. If the affected blood vessels are small, the blood may slowly seep into the digestive tract. Over a long period of time, a person may become anemic and feel weak, dizzy, or tired. If a damaged blood vessel is large, bleeding is dangerous and requires prompt medical attention. Symptoms include feeling weak and dizzy when standing, vomiting blood, or fainting. The stool may become a tarry black color from the blood. Most bleeding ulcers can be treated endoscopically. The ulcer is located and the blood vessel is cauterized with a heating device or injected with material to stop bleeding. If endoscopic treatment is unsuccessful, surgery may be required.

Sometimes an ulcer eats a hole in the wall of the stomach or duodenum. Bacteria and partially digested food can spill through the opening into the sterile abdominal cavity (peritoneum). This causes peritonitis, an inflammation of the abdominal cavity and wall. A perforated ulcer that can cause sudden, sharp, severe pain usually requires immediate hospitalization and surgery.

Ulcers located at the end of the stomach where the duodenum is attached, can cause swelling and scarring, which can narrow or close the intestinal opening. This obstruction can prevent food from leaving the stomach and entering the small intestine. As a result, a person may vomit the contents of the stomach. Endoscopic balloon dilation, a procedure that uses a balloon to force open a narrow passage, may be performed. If the dilation does not relieve the problem, then surgery may be necessary.

Gastroesophageal Reflux Disease

Gastroesophageal reflux disease (GERD) (also called peptic esophagitis and reflux esophagitis) is an inflammation of the esophagus resulting from regurgitation of gastric contents into the esophagus. Some gastroesophageal reflux is a normal condition that often occurs without symptoms after meals. However, the reflux can be become more serious when it is due to an incompetent (weakened) lower esophageal sphincter, a band of muscle fibers that closes off the esophagus from the stomach. When this occurs, acidic or alkaline gastric contents from the stomach can return to the esophagus through the lower esophageal sphincter and cause the symptoms of GERD. Conditions which can cause an incompetent esophageal sphincter with resulting s GERD include pregnancy, hiatal hernia, obesity, recurrent or persistent vomiting, and nasogastric tubes. GERD is also a risk factors of esophageal surgery and esophageal stricture.

The symptoms of GERD include heartburn, belching, regurgitation of food, nausea, vomiting, hoarseness of voice, sore throat, difficulty swallowing and cough. Diagnostic of GERD is stool positive for guaiac, continuous esophageal pH monitoring showing reflux, endoscopy showing esophagitis or ulceration, esophageal manometry showing abnormal sphincter pressure, a barium swallow showing reflux, and a positive Bernstein test for gastric acid reflux Treatment for GERD measures include weight reduction, avoiding lying down after meals, sleeping with the head of the bed elevated, taking medication with plenty of water, avoiding dietary fat, chocolate, caffeine, peppermint (these can cause lower esophageal pressure), avoiding alcohol and tobacco. Medications that can alleviate symptoms of GERD include antacids after meals and at bedtime, histamine H2 receptor blockers, promotility agents, proton pump inhibitors. Furthermore, anti-reflux operations (Nissen fundoplication) may be indicated for a patients with pharmacologically intractable GERD. Untreated GERD can result in esophagitis, esophageal ulcer, bronchospasm, chronic pulmonary disease and Barrett's esophagus, the latter being a change in the lining of the esophagus that can increase the risk of cancer.

Thus, there are numerous deficiencies and drawbacks associated with the current therapies for both peptic ulcers and for gastro esophageal reflux disease.

Botulinum Toxin

The genus Clostridium has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1996) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71–85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$, was originally thought to cleave syntaxin, but was found to cleave syntaxin and SNAP-25. Each of the botulinum toxins specifically cleaves a different bond, except botulinum toxin type B (and tetanus toxin) which cleave the same bond.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Gonelle-Gispert, C., et al., *SNAP-25a and-25b isoforms are both expressed in insulin-secreting cells and can function in insulin secretion*, Biochem J. 1;339 (pt 1):159–65:1999, and Boyd R. S. et al., *The effect of botulinum neurotoxin-B on insulin release from a ∃-cell line*, and Boyd R. S. et al., *The insulin secreting ∃-cell line, HIT-15, contains SNAP-25 which is a target for botulinum neurotoxin-A*, both published at *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$, is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for a lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy.

Botulinum toxins and toxin complexes can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St. Louis, Mo. Commercially available botulinum toxin containing pharmaceutical compositions include BOTOX® (Botulinum toxin type A neurotoxin complex with human serum albumin and sodium chloride) available from Allergan, Inc., of Irvine, Calif. in 100 unit vials as a lyophilized powder to be reconstituted with 0.9% sodium chloride before use), Dysport® (*Clostridium botulinum* type A toxin haemagglutinin complex with human serum albumin and lactose in the formulation), available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Elan Corporation, Dublin, Ireland).

The success of botulinum toxin type A to treat a variety of clinical conditions has led to interest in other botulinum toxin serotypes. Additionally, pure botulinum toxin has been used to treat humans. See e.g. Kohl A., et al., *Comparison of the effect of botulinum toxin A (Botox (R)) with the highly-purified neurotoxin (NT201) in the extensor digitorum brevis muscle test*, Mov Disord 2000;15(Suppl 3):165. Hence, a pharmaceutical composition can be prepared using a pure botulinum toxin.

The type A botulinum toxin is known to be soluble in dilute aqueous solutions at pH 4–6.8. At pH above about 7 the stabilizing nontoxic proteins dissociate from the neurotoxin, resulting in a gradual loss of toxicity, particularly as the pH and temperature rise. Schantz E. J., et al *Preparation and characterization of botulinum toxin type A for human treatment* (in particular pages 44–45), being chapter 3 of Jankovic, J., et al, *Therapy with Botulinum Toxin*, Marcel Dekker, Inc (1994).

The botulinum toxin molecule (about 150 kDa), as well as the botulinum toxin complexes (about 300–900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51 (2);522–527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675–681:1987. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9);1373–1412 at 1393; Bigalke H., et al., *Botulinum A Neurotoxin Inhibits Non-Cholinergic Synaptic Transmission in Mouse Spinal Cord Neurons in Culture*, Brain Research 360;318–324:1985; Habermann E., *Inhibition by Tetanus and Botulinum A Toxin of the release of [$^3$H]Noradrenaline and [$^3$H]GABA From Rat Brain Homogenate*, Experientia 44;224–226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244–251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botulinum toxin and Other Microbial Neurotoxins in Medicine*, Microbiol Rev. 56;80–99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ LD$_{50}$ U/mg or greater; purified botulinum toxin type B with an approximately 156 kD molecular weight with a specific potency of $1-2 \times 10^8$ LD$_{50}$ U/mg or greater, and; purified botulinum toxin type F with an approximately 155 kD molecular weight with a specific potency of $1-2 \times 10^7$ LD$_{50}$ U/mg or greater.

Either the pure botulinum toxin (i.e. the 150 kilodalton botulinum toxin molecule) or the toxin complex can be used to prepare a pharmaceutical composition. Both molecule and complex are susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249–53: 1997.

Botulinum toxins have been used in clinical settings for the treatment of neuromuscular disorders characterized by hyperactive skeletal muscles. Botulinum toxin type A (Botox®) was approved by the U.S. Food and Drug Administration in 1989 for the treatment of essential blepharospasm, strabismus and hemifacial spasm in patients over the age of twelve. In 2000 the FDA approved commercial preparations of type A (Botox®) and type B botulinum toxin (MyoBloc™) serotypes for the treatment of cervical dystonia, and in 2002 the FDA approved a type A botulinum toxin (Botox®) for the cosmetic treatment of certain hyperkinetic (glabellar) facial wrinkles. Clinical effects of peripheral intramuscular botulinum toxin type A are usually seen within one week of injection and sometimes within a few hours. The typical duration of symptomatic relief (i.e. flaccid muscle paralysis) from a single intramuscular injection of botulinum toxin type A can be about three months, although in some cases the effects of a botulinum toxin induced denervation of a gland, such as a salivary gland, have been reported to last for several years. For example, it is known that botulinum toxin type A can have an efficacy for up to 12 months (Naumann M., et al., *Botulinum toxin type A in the treatment of focal, axillary and palmar hyperhidrosis and other hyperhidrotic conditions*, European J. Neurology 6 (Supp 4): S111–S115:1999), and in some circumstances for as long as 27 months. Ragona, R. M., et al., *Management of parotid sialocele with botulinum toxin*, The Laryngoscope 109:1344–1346:1999. However, the usual duration of an intramuscular injection of Botox® is typically about 3 to 4 months.

It has been reported that a botulinum toxin type A has been used in diverse clinical settings, including for example as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
   (a) flexor digitorum profundus: 7.5 U to 30 U
   (b) flexor digitorum sublimus: 7.5 U to 30 U
   (c) flexor carpi ulnaris: 10 U to 40 U
   (d) flexor carpi radialis: 15 U to 60 U
   (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Lyons, J., et al., *Tremor-Predominant Parkinson's Disease*, Drugs & Aging 16(4);273–278:2000.

Treatment of certain gastrointestinal and smooth muscle disorders with a botulinum toxin are known. See e.g. U.S. Pat. Nos. 5,427,291 and 5,674,205 (Pasricha). Additionally, transurethral injection of a botulinum toxin into a bladder sphincter to treat a urination disorder is known (see e.g. Dykstra, D. D., et al, *Treatment of detrusor-sphincter dyssynergia with botulinum A toxin: A double-blind study*, Arch Phys Med Rehabil 1990 January;71:24–6), as is injection of a botulinum toxin into the prostate to treat prostatic hyperplasia. See e.g. U.S. Pat. No. 6,365,164 (Schmidt).

U.S. Pat. No. 5,766,605 (Sanders) proposes the treatment of various autonomic disorders, such as hypersalivation and rhinittis, with a botulinum toxin. Additionally, it is known that nasal hypersecretion is predominantly caused by over activity of nasal glands, which are mainly under cholinergic control and it has been demonstrated that application of botulinum toxin type A to mammalian nasal mucosal tissue of the maxillary sinus turbinates can induce a temporary apoptosis in the nasal glands. Rohrbach S., et al., *Botulinum toxin type A induces apoptosis in nasal glands of guinea pigs*, Ann Otol Rhinol Laryngol 2001 November;110(11): 1045–50. Furthermore, local application of botulinum toxin A to a human female patient with intrinsic rhinitis resulted in a clear decrease of the nasal hypersecretion within five days. Rohrbach S., et al., *Minimally invasive application of botulinum toxin type A in nasal hypersecretion*, J Oto-Rhino-Laryngol 2001 November–December;63(6):382–4.

Various afflictions, such as hyperhydrosis and headache, treatable with a botulinum toxin are discussed in WO 95/17904 (PCT/US94/14717) (Aoki). EP 0 605 501 B1 (Graham) discusses treatment of cerebral palsy with a botulinum toxin and U.S. Pat. No. 6,063,768 (First) discusses treatment of neurogenic inflammation with a botulinum toxin.

In addition to having pharmacologic actions at the peripheral location, botulinum toxins can also have inhibitory effects in the central nervous system. Work by Weigand et al, ($^{125}I$-labelled botulinum A neurotoxin:pharmacokinetics in cats after intramuscular injection, Nauny-Schmiedeberg's Arch. Pharmacol. 1976; 292,161–165), and Habermann, ($^{125}I$-labelled Neurotoxin from clostridium botulinum A: preparation, binding to synaptosomes and ascent to the spinal cord, Nauny-Schmiedeberg's Arch. Pharmacol. 1974; 281, 47–56) showed that botulinum toxin is able to ascend to the spinal area by retrograde transport. As such, a botulinum toxin injected at a peripheral location, for example intramuscularly, may be retrograde transported to the spinal cord.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

A botulinum toxin has also been proposed for the treatment of hyperhydrosis (excessive sweating, U.S. Pat. No. 5,766,605), headache, (U.S. Pat. No. 6,458,365, migraine headache (U.S. Pat. No. 5,714,468), post-operative pain and visceral pain (U.S. Pat. No. 6,464,986), pain by intraspinal administration (U.S. Pat. No. 6,113,915), Parkinson's disease by intracranial administration (U.S. Pat. No. 6,306, 403), hair growth and hair retention (U.S. Pat. No. 6,299, 893), psoriasis and dermatitis (U.S. Pat. No. 5,670,484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437,291, including injection of a botulinum toxin into the upper and lower esophageal, pyloric and anal sphincters) ), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977). Additionally, controlled release toxin implants are known (U.S. Pat. Nos. 6,306,423 and 6,312,708).

It has been reported that that intravenous injection of a botulinum toxin causes a decline of pentagastrin stimulated acid and pepsin secretion in rats. Kondo T., et al., *Modification of the action of pentagastrin on acid secretion by botulinum toxin*, Experientia 1977;33:750–1. Additionally it has been speculated that a botulinum toxin can be used to reduce a gastrointestinal secretion, such as a gastric secretion. See pages 16–17 of WO 95/17904. Furthermore, a botulinum toxin has been proposed for the treatment of disorders of gastrointestinal muscle in the enteric nervous system disorder (U.S. Pat. No. 5,437,291) and well as to treat various autonomic disorders (U.S. Pat. No. 5,766,605). Botulinum toxin has been injected into the fundus of the stomach of dogs. Wang Z., et al., *Effects of botulinum toxin on gastric myoelectrical and vagal activities in dogs*, Gastroenterology 2001 April;120(5 Suppl 1):A-718. Additionally, intramuscular injection of a botulinum toxin into the gastric antrum has been proposed as a treatment for obesity. See e.g. Gui D., et al., *Effects of botulinum toxin on gastric emptying and digestive secretions. A possible tool for correction of obesity?,* Naunyn Schmiedebergs Arch Pharmacol 2002 June;365(Suppl 2):R22; Albanese A., et al., *The use of botulinum toxin on smooth muscles*, Eur J Neurol 1995 November;2(Supp 3):29–33, and; Gui D., et al., *Botulinum toxin injected in the gastric wall reduces body weight and food intake in rats*, Aliment Pharmacol Ther 2000 June;14 (6):829–834. Furthermore, botulinum toxin type A has been proposed as a therapeutic application for the control of secretion in the stomach. Rossi S., et al., *Immunohistochemical localization of SNAP-25 protein in the stomach of rat*, Naunyn Schmiedebergs Arch Pharmacol 2002;365(Suppl 2):R37.

Significantly, it has been reported that injection of a botulinum toxin into the lower esophageal sphincter for the treatment of achalasia results in the formation of ulcers in the esophagus. Eaker, E. Y., et al., *Untoward effects of esophageal botulinum toxin injection in the treatment of achalasia*, Dig Dis Sci 1997 April;42(4):724–7. It is know to inject a botulinum toxin into a spastic pylorid sphincter of a patient with a prepyloric ulcer in order to permit the pyloric muscle to open. Wiesel P. H. et al., *Botulinum toxin for refractory postoperative pyloric spasm*, Endoscopy 1997;29 (2):132.

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of Clostridium (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153–9158:1990.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore are methods for treating peptic ulcers and for treating gastroesophageal reflux disease with a botulinum toxin.

SUMMARY

Figure 1:
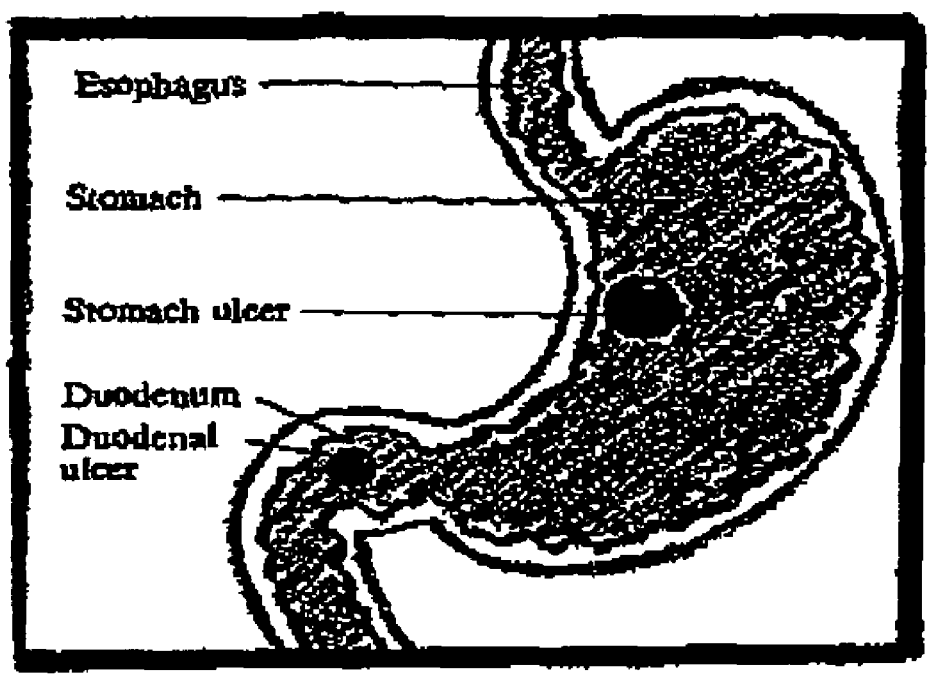
FIG. 1 is a drawing which illustrates exemplary locations of gastric (stomach) and duodenal ulcers.

The present invention meets this need and provides methods for treating peptic ulcers and for treating gastroesophageal reflux disease with a botulinum toxin. The present invention excludes intramuscular or subcutaneous injection of a botulinum toxin to treat an ulcer or for treating gastroesophageal reflux disease because such methods are invasive (i.e. endoscopy) and inconvenient for patients.

According to the present invention, the botulinum toxin is compounded as an oral formulation for release of the toxin active ingredient in the stomach or duodenum of a patient with a peptic ulcer. Preparation of an oral formulation of a botulinum toxin can be easily accomplished by mixing a lyophilized or freeze dried botulinum toxin powder with a carrier such as flour, sugar or gelatin and then compressing the mixture to make an ingestible tablet. The carrier and the amount of compression is chosen so the resulting tablet (or alternately a capsule or gelcap containing a therapeutic amount of the toxin mixed with or without a carrier can be formulated) is intended to be swallowed and the carrier and the characteristics of the carrier are such that the carrier rapidly dissolves in the stomach, freeing the botulinum toxin active ingredient.

The botulinum toxin is one of the botulinum toxin types A, B, $C_1$, D, E, F and G and is preferably botulinum toxin type A. The botulinum toxin can be associated with the carrier in an amount of between about 1 unit and about 10,000 units of the botulinum toxin. Preferably, the quantity of the botulinum toxin associated with the carrier is between about 5 units and about 500 units of a botulinum toxin type A. Where the botulinum toxin is botulinum toxin type B, preferably, the quantity of the botulinum toxin associated with the carrier can be between about 250 units and about 25,000 units of a botulinum toxin type B.

A detailed embodiment of the present invention can comprise an oral formulation comprising a rapidly biodegradable polymer or natural substance (i.e. floor, sugar or gelatin) and between about 5 units and about 25,000 units of a botulinum toxin encapsulated by the carrier, thereby forming a controlled release system, wherein therapeutic amounts of the botulinum toxin can be released from the carrier in the gastrointestinal system of a human patient with a peptic ulcer.

A method for making a botulinum toxin ingestible tablet or capsule within the scope of the present invention can have the steps of: mixing or dispersing a botulinum toxin in a suitable carrier to form a carrier-botulinum toxin mixture, and; compressing the carrier-botulinum toxin mixture into a tablet or filling the mixture into a capsule.

An alternate embodiment of the present invention can be a carrier comprising a polymer selected from the group of polymers consisting of rapidly biodegradable polylactides and polyglycolides and a stabilized botulinum toxin associated with the carrier, thereby forming a botulinum toxin delivery system, wherein therapeutic amounts of the botulinum toxin can be released from the carrier in a patients GI system upon oral ingestion. The carrier can comprise a plurality of botulinum toxin incorporating microspheres.

The botulinum toxin used to prepare an oral formulation according to the present invention can comprise: a first element comprising a binding element able to specifically bind to a neuronal cell surface receptor under physiological conditions, a second element comprising a translocation element able to facilitate the transfer of a polypeptide across a neuronal cell membrane, and a third element comprising a therapeutic element able, when present in the cytoplasm of a neuron, to inhibit exocytosis of acetylcholine from the neuron. The therapeutic element can cleave a SNARE protein, thereby inhibiting the exocytosis of acetylcholine from the neuron and the SNARE protein is can be selected from the group consisting of syntaxin, SNAP-25 and VAMP. Generally, the neuron affected by the botulinum toxin is a presynaptic, cholinergic neuron which innervates e.g. a GI tract muscle (smooth, striated or mixed smooth and striated GI muscle) or a GI tract secretory glandular tissue. Although a cholinergic neuron can show high affinity for a botulinum toxin (i.e. through a receptor for the toxin), muscle cells and gland cells can directly take up the toxin through a low affinity mechanism (i.e. pinocytosis). Thus, both neurons and non-neuronal cell can be targets for the botulinum toxin.

The amount of a botulinum toxin administered by an oral formulation within the scope of the present invention during a given period can be between about $10^{-3}$ U/kg and about 35 U/kg for a botulinum toxin type A and up to about 2000 U/kg for other botulinum toxins, such as a botulinum toxin type B. 35 U/kg or 2000 U/kg is an upper limit because it approaches a lethal dose of certain neurotoxins, such as botulinum toxin type A or botulinum toxin type B, respectively. Thus, it has been reported that about 2000 units/kg of a commercially available botulinum toxin type B preparation approaches a primate lethal dose of type B botulinum toxin. Meyer K. E. et al, *A Comparative Systemic Toxicity Study of Neurobloc in Adult Juvenile Cynomolgus Monkeys*, Mov. Disord 15(Suppl 2);54;2000.

Preferably, the amount of a type A botulinum toxin administered by a oral formulation is between about $10^{-2}$ U/kg and about 25 U/kg. Preferably, the amount of a type B botulinum toxin administered by a oral formulation during a given period is between about $10^{-2}$ U/kg and about 1000 U/kg, since it has been reported that less than about 1000 U/kg of type B botulinum toxin can be intramuscularly administered to a primate without systemic effect. Ibid. More preferably, the type A botulinum toxin is administered in an amount of between about $10^{-1}$ U/kg and about 15 U/kg. Most preferably, the type A botulinum toxin is administered in an amount of between about 1 U/kg and about 10 U/kg. In many instances, an administration of from about 1 units to about 500 units of a botulinum toxin type A, provides effective and long lasting therapeutic relief. More preferably, from about 5 units to about 300 units of a botulinum toxin, such as a botulinum toxin type A, can be used and most preferably, from about 10 units to about 200 units of a neurotoxin, such as a botulinum toxin type A, can be locally administered into a target tissue with efficacious results. In a particularly preferred embodiment of the present invention from about 1 units to about 100 units of a botulinum toxin, such as botulinum toxin type A, can be locally administered into a target tissue with therapeutically effective results.

The botulinum toxin can be made by *Clostridium botulinum*. Additionally, the botulinum toxin can be a modified botulinum toxin that is, a botulinum toxin that has at least one of its amino acids deleted, modified or replaced, as compared to the native or wild type botulinum toxin. Furthermore, the botulinum toxin can be a recombinant produced botulinum toxin or a derivative or fragment thereof.

Significantly, the botulinum toxin can is administered by oral ingestion (i.e. by swallowing the tablet or capsule) by a patient with a peptic ulcer by placement of a botulinum toxin oral formulation. Where the botulinum toxin is botulinum toxin type A, the amount of orally administered botulinum toxin can be between about 1 unit and about 500 units, preferable between 10 and 300 units and most preferably between 50 and 200 units of botulinum toxin type A.

Notably, it has been reported that glandular tissue treated by a botulinum toxin can show a reduced secretory activity for as long as 27 months post injection of the toxin. *Laryngoscope* 1999; 109:1344–1346, *Laryngoscope* 1998; 108:381–384.

Definitions

The following definitions apply herein.

"About" means plus or minus ten percent of the value so qualified.

"Biocompatible" means that there is an insignificant inflammatory response from use of the oral formulation.

"Biologically active compound" means a compound which can effect a beneficial change in the subject to which it is administered. For example, "biologically active compounds" include neurotoxins.

"Effective amount" as applied to the biologically active compound means that amount of the compound which is generally sufficient to effect a desired change in the subject. For example, where the desired effect is a healing of a peptic ulcer, an effective amount of the compound is that amount which causes at least a substantial healing of the ulcer, and without resulting in a significant systemic toxicity reaction.

"Effective amount" as applied to a non-active ingredient constituent of an oral formulation (such as a carrier used for mixing with a botulinum toxin) refers to that amount of the non-active ingredient constituent which is sufficient to positively influence the release of a biologically active agent at a desired rate for a desired period of time in the GI tract. This "effective amount" can be determined based on the teaching in this specification and the general knowledge in the art.

"Neurotoxin" means an agent which can interrupt nerve impulse transmission across a neuromuscular or neuroglandular junction, block or reduce neuronal exocytosis of a neurotransmitter or alter the action potential at a sodium channel voltage gate of a neuron. Examples of neurotoxins include botulinum toxins, tetanus toxins, saxitoxins, and tetrodotoxin.

"Treatment" means any treatment of a disease in a mammal, and includes: (i) preventing the disease from occurring or; (ii) inhibiting the disease, i.e., arresting its development; (iii) relieving the disease, i.e., reducing the incidence of symptoms of or causing regression of the disease.

A method of using an oral formulation within the scope of the present invention can comprise providing a therapeutically effective level in the GI tract of biologically active, neurotoxin in a patient for a upon ingestion of an oral botulinum toxin formulation by the patient.

Generally, the present invention encompasses a method for treating a peptic ulcer by administering a botulinum toxin to thereby treat a gastric ulcer. The botulinum toxin can be selected from the group consisting of botulinum toxins types A, B, C, D, E, F and G and the peptic ulcer can be a gastric ulcer or a duodenal ulcer.

The administration of the toxin is by oral ingestion of the botulinum toxin to a patient with a peptic ulcer and the botulinum toxin is administered in a therapeutically effective amount. A detailed embodiment of the present invention can encompass a method for treating a peptic ulcer by oral ingestion by a patient with a peptic ulcer of a therapeutically effective amount of a botulinum toxin type A. The present invention also encompasses a method for treating a gastroesophageal reflux disease by oral ingestion by a patient with a gastric acid reflux disorder of a botulinum toxin.

A botulinum toxin oral formulation within the scope of the present invention can comprise a botulinum toxin and a carrier associated with the botulinum toxin, thereby forming a botulinum toxin oral formulation, wherein the carrier is formulated to release therapeutic amounts of the botulinum toxin in a gastrointestinal tract of a patient with a gastric ulcer without a significant immune system response. In this preferably, substantial amounts of the botulinum toxin has not be transformed into a botulinum toxoid prior to association of the botulinum toxin with the carrier. Thus, significant amounts of the botulinum toxin associated with the carrier have a toxicity which is substantially unchanged relative to the toxicity of the botulinum toxin prior to association of the botulinum toxin with the carrier.

Additionally, in such an oral formulation the carrier can comprise a biocompatible, biodegradable substance selected from the group consisting of flour, sugar and gelatin. The botulinum toxin associated with the carrier can be between about 1 unit and about 10,000 units of the botulinum toxin.

A detailed oral formulation within the scope of the present invention can comprise a botulinum toxin which has: a first element comprising a binding element able to specifically bind to a neuronal cell surface receptor under physiological conditions; a second element comprising a translocation element able to facilitate the transfer of a polypeptide across a neuronal cell membrane, and; a third element comprising a therapeutic element able, when present in the cytoplasm of a neuron, to inhibit exocytosis of acetylcholine from the neuron.

An alternate embodiment within the scope of the present invention can comprise a botulinum toxin type A and a carrier associated with the botulinum toxin type A, thereby forming a botulinum toxin oral formulation, wherein the carrier is formulated to release therapeutic amounts of the botulinum toxin type A in a gastrointestinal tract of a patient with a gastric ulcer without a significant immune system response, and wherein the carrier comprises a biocompatible, biodegradable substance selected from the group consisting of flour, sugar and gelatin.

DESCRIPTION

The present invention is based upon the discovery of a peptic ulcer can be successfully treated with an oral formulation of a botulinum toxin. The present invention is also based upon the discovery that gastroesophageal reflux disease can be treated with an oral formulation of a botulinum toxin. Thus, I have discovered that ingestion of a botulinum toxin, such as a botulinum toxin type A, mixed with a suitable carrier which dissolves in the stomach or upper intestine permits delivery of therapeutic amounts of a bioactive botulinum toxin to and to the vicinity of a peptic ulcer. This permits a reduction of excessive or damaging gastric secretions from and from the vicinity of the peptic ulcer. Typically, within a few days thereafter the ulcer shows unmistakable signs of healing (ulcer remission) and the ulcer can be completely cured within a few weeks after administration of the oral botulinum toxin formulation. Additionally, I have discovered that within a few days after the oral toxin administration, the symptoms of GERD subside due to a reduction of gastric secretions due to the orally administered botulinum toxin. Side effects can include a reduced motility of gastrointestinal muscles and transient weight loss.

My discovery that an orally administered botulinum toxin can be used to treat a peptic ulcer and/or GERD is surprising because it has been reported that injection of a botulinum toxin into the lower esophageal sphincter for the treatment of achalasia can actually result in the formation of ulcers in the esophagus (Eaker, E. Y., et al., *Untoward effects of esophageal botulinum toxin injection in the treatment of achalasia*, Dig Dis Sci 1997 April;42(4):724–7).

The therapeutic dose of orally administered botulinum toxin is such that there are nominal or insignificant systemic effects due to any botulinum toxin which is absorbed through the gut lining into the circulatory system. Thus, 200 units of botulinum toxin can be injected into the pyloric (lower stomach) sphincter of patients with diabetic gastroparesis without any ensuing systemic toxicity. Crowell, M. D., et al., *Botulinum toxin reduces pyloric dysfunction in patients with diabetic gastroparesis*, Gastroenterology 2002 April;122(4 Supp 1):A451–A452. Although there is no evidence for a teratogenic effect by a botulinum toxin, methods within the scope of my invention disclosed herein are not intended for application to or by a patient who is pregnant, nursing or who intends to become pregnant during the treatment period.

Without wishing to be bound by theory, a physiological mechanism can be proposed for the efficacy of the present invention. Thus, it is well known that botulinum toxin acts on cholinergic nerves, including those in the gastrointestinal tract responsible for the motility of GI muscles. Pasricha, P. J., *Botulinum toxin for spastic gastrointestinal disorders*, Bailliere's Clin Gastroenterol 1999;13(1):131–143. Additionally, gastrin secretion and HCL production by gastric parietal cells is strongly dependant upon cholinergic activity of vagal and myenteric fibers which act on neuroglandular junctions in the gastrointestinal tract. Rossi S., et al., *Immunohistochemical localization of SNAP-25 protein in he stomach of rat*, Naunyn Schmiedebergs Arch Pharmacol 2002; 365(Suppl 2):R37. Furthermore, the intracellular substrate (SNAP-25) for botulinum toxin type A BTX-A is present in stomach wall cells. Gui D., et al., *Effects of botulinum toxin on gastric emptying and digestive secretions. A possible tool for correction of obesity?*, Naunyn Schmiedebergs Arch Pharmacol 2002 June;365(Suppl 2):R22. Finally, it is well know that ulcer formation is due to or is contributed to by excessive gastrin secretion by stomach wall cells and that botulinum toxin. Thus, an oral formulation of a botulinum toxin can be used to treat a peptic ulcer by downregulating excessive stomach acid secretions and thereby permitting an ulcer to heal.

It appears clear that an orally administered botulinum toxin can remain bioactive in the harsh environment of the GI tract. Thus, botulinum toxin is secreted by a Clostridial bacterium as a complex which comprises the approximately 150 kDa single chain protein toxin molecule surrounded by a number of non-toxin protein molecules. Significantly, the non toxin proteins act to protect the toxin from acid hydrolysis and enzymatic degradation during passage of the complex through the GI tract, so that the toxin complex is able to survive the harsh conditions of extremes of pH and proteolytic enzymes and yet still function as a highly potent neurotoxin. It has been demonstrated that the non-toxin proteins which are complexed with the botulinum toxin molecule act to protect the 150 kDA toxin molecule in the gastrointestinal tract from digestive acids. Hanson, M. A. et al., *Structural view of botulinum neurotoxin in numerous functional states*, being chapter 2, pages 11–27 of Brin M. F. et al, editors, *Scientific and therapeutic aspects of botulinum Toxin*, Lippincott, Williams & Wilkins (2002).

A botulinum toxin delivery system within the scope of the present invention is capable of releasing a therapeutic amount of a botulinum toxin into the GI tract of a patient with a peptic ulcer, as shown by FIG. 1. The amount of released botulinum toxin can comprise (for a botulinum toxin type A) as little as about 10 units (i.e. to treat a small ulcer in an infant) to as much as 500 units (i.e. to treat multiple peptic ulcers in a large adult. The quantity of botulinum toxin required for therapeutic efficacy can be varied according to the known clinical potency of the different botulinum toxin serotypes. For example, several orders of magnitude more units of a botulinum toxin type B are typically required to achieve a physiological effect comparable to that achieved from use of a botulinum toxin type A.

The botulinum toxin released in a therapeutically effective amount by a oral formulation within the scope of the present invention is preferably, substantially biologically active botulinum toxin. In other words, the botulinum toxin released by the disclosed oral formulation in the GI tract of a patient is capable of binding with high affinity to a cholinergic neuron, being translocated, at least in part, across the neuronal membrane, and through its activity in the cytosol of the neuron of inhibiting exocytosis of acetylcholine from the neuron. The purpose of the present invention is to permit release in the GI tract of a botulinum toxin from a oral formulation so as to inhibit exocytosis in vivo and thereby achieve a desired therapeutic effect, that is the healing of an ulcer.

The oral formulation is prepared so that the botulinum toxin is substantially uniformly dispersed in a biodegradable carrier. The thickness of the oral formulation can be used to control the absorption of water by, and thus the rate of release of a neurotoxin from, a composition of the invention, thicker tablets of capsules releasing the polypeptide more slowly than thinner ones. The carrier is preferably comprised of a non-toxic, non-immunological, biocompatible material.

Release of biologically active neurotoxin from, an oral formulation of the present invention results in therapeutically effective, with negligible serum levels, of biologically active, neurotoxin. Preferably, the release of biologically active neurotoxin in vivo in the GI tract does not result in a significant immune system response.

The neurotoxin oral formulation of my invention can be formed into many shapes such as a film, a pellet, a cylinder or disc.

The specific dosage by oral formulation appropriate for administration is readily determined by one of ordinary skill in the art according to the factors discussed above. The dosage can also depend upon the size of the tissue mass to be treated or denervated, and the commercial preparation of the toxin. Additionally, the estimates for appropriate dosages in humans can be extrapolated from determinations of the amounts of botulinum required for effective denervation of other tissues. Thus, the amount of botulinum A to be injected is proportional to the mass and level of activity of the tissue to be treated. Generally, between about 0.01 units per kilogram to about 35 units per kg of patient weight of a botulinum toxin, such as botulinum toxin type A, can be released by the present oral formulation to effectively accomplish a desired ulcer healing. Less than about 0.01 U/kg of a botulinum toxin does not have a significant therapeutic effect upon a muscle, while more than about 35 U/kg of a botulinum toxin approaches a toxic dose of a neurotoxin, such as a botulinum toxin type A. Careful preparation of the oral formulation prevents significant amounts of a botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the tissue to be treated and the administration route chosen. Botulinum toxin type A is a preferred botulinum toxin serotype for use in the methods of the present invention.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known safe and efficacious use for the treatment of skeletal muscle and smooth muscle disorders when locally administered by intramuscular injection.

The present invention includes within its scope the use of any neurotoxin which has a long duration therapeutic effect when used to treat a peptic ulcer. For example, neurotoxins made by any of the species of the toxin producing Clostridium bacteria, such as *Clostridium botulinum*, *Clostridium butyricum*, and *Clostridium beratti* can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention by the method disclosed herein can cause a peptic ulcer to heal and disappear.

The present invention includes within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for a cell surface receptor present on a cell.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

Methods for determining the appropriate dosage is generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

Also within the scope of the present invention is an oral formulation in the form of a suspension for ingestion prepared by suspending the neurotoxin encapsulated microspheres in a suitable liquid, such as physiological saline.

EXAMPLES

The following examples set forth specific compositions and methods encompassed by the present invention and are not intended to limit the scope of the present invention.

Example 1

Method for Making a Botulinum Toxin Tablet for Oral Ingestion

A botulinum toxin can be compounded as an oral formulation for release of the toxin active ingredient in the stomach or duodenum. This is easily accomplished by mixing with a mortar and pestle (at room temperature without addition of any water or saline) 50 units of a commercially available lyophilized botulinum toxin powder, such as non-reconstituted BOTOX® (or 200 units of DYSPORT® powder) with a biodegradable carrier such as flour or sugar. Alternately, the botulinum toxin can be mixed by homogenization or sonication to form a fine dispersion of the powdered toxin in the carrier. The mixture can then compressed with a tablet making machine (such as the tablet press available from Scheu & Kniss, 1500 W. Ormsby Ave, Louisville, Ky. 40210) to make an ingestible tablet. Alternately, the toxin can be formulated with gelatin by well known methodologies to make an ingestible geltab.

Example 2

Method for Treating a Peptic Ulcer

A 52 year old male presents with a burning pain in the abdomen between the breastbone and the navel and he relates that the pain often occurs between meals and in the early hours of the morning. The patient also complains of nausea and loss of appetite. Endoscopy, supplemented by barium x-ray, confirms the presence of a gastric ulcer. The ulcer proves intractable to H2-blockers as well as to antibiotics to *H. pylori*. The patient is treated by administration of the botulinum toxin oral formulation of Example 1. Thus, the patient swallows one 50 units type A tablet during each of four days. Within two weeks the symptoms of a peptic ulcer have disappeared and endoscopy reveals no trace of the ulcer.

Example 3

Method for Treating Gastroesophageal Reflux Disease

A 62 year old obese female is admitted with symptoms of heartburn, near continuous belching, regurgitation, sore throat, difficulty swallowing and cough. Work up indicates esophagitis and esophageal manometry points to low (lower esophageal sphincter (LES) pressure. The Bernstein test for gastric acid reflux is positive. Thus, a diagnosis of GERD is made. The patient has been unsuccessful in various weight loss programs and regularly ingests chocolates, and smokes heavily. Antacids and histamine H2 receptor blockers have been ineffective. The patient is treated by administration of the botulinum toxin oral formulation of Example 1. Thus, the patient swallows one 2000 unit type B tablet during each of four days. Within two weeks the symptoms of GERD have disappeared or been substantially reduced.

Compositions and methods according to the invention disclosed herein has many advantages, including the following:

1. a botulinum toxin oral formulation can be used to provide therapeutically effective treatment of a peptic ulcer.
2. reduced need for patient follow up care.
3. increased patent comfort due to the removal of the need for any injections.
4. improved patient compliance.

An advantage of the present oral formulations for neurotoxins include long term ulcer remission.

All references, articles, publications and patents and patent applications cited herein are incorporated by reference in their entireties.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes oral formulations wherein two or more neurotoxins, such as two or more botulinum toxins, are administered concurrently or consecutively. For example, botulinum toxin type A can be administered by an oral formulation until a loss of clinical response or neutralizing antibodies develop, followed by administration via oral formulation of a botulinum toxin type B or E. Alternately, a combination of any two or more of the botulinum serotypes A–G can be locally administered to control the onset and duration of the desired therapeutic result. Furthermore, non-neurotoxin compounds can be administered prior to, concurrently with or subsequent to administration of the neurotoxin oral formulation so as to provide an adjunct effect such as enhanced or a more rapid onset of denervation before the neurotoxin, such as a botulinum toxin, begins to exert its therapeutic effect.

The present invention also includes within its scope the use of a neurotoxin, such as a botulinum toxin, in the preparation of a medicament as an oral formulation for the treatment of a peptic ulcer.

Accordingly, the spirit and scope of the following claims should not be limited to the descriptions of the preferred embodiments set forth above.

I claim:

1. A method for treating gastroesophageal reflux disease, the method comprising the step of oral ingestion of a therapeutically effective amount of a botulinum toxin by a patient with gastroesophageal reflux disease, thereby reducing a symptom of the gastroesophageal reflux disease, wherein the symptom is selected from the group consisting of heartburn, belching, regurgitation of food, nausea, vomiting, hoarseness of voice, sore throat, difficulty swallowing and cough, wherein the amount of the botulinum toxin is from about 50 to about 2000 units.

2. The method of claim 1, wherein the botulinum toxin is selected from the group consisting of botulinum toxin types A, B, $C_1$, D, E, F and G.

3. The method of claim 1, wherein the botulinum toxin is botulinum toxin type A.

4. The method of claim 1, wherein the botulinum toxin is botulinum toxin type B.

5. The method of claim 1, wherein the therapeutically effective amount of a botulinum toxin is provided in the form of a tablet or capsule or geltab.

6. The method of claim 1, wherein the symptom is reduced within two weeks of oral ingestion of the therapeutically effective amount of a botulinum toxin.

7. A method for treating a gastroesophageal reflux disease, the method comprising the step of oral ingestion of a therapeutically effective amount of a botulinum toxin by a patient with gastroesophageal reflux disease, thereby reducing a symptom of the gastroesophageal reflux disease, wherein the symptom is selected from the group consisting of heartburn, belching, regurgitation of food, nausea, vomiting, hoarseness of voice, sore throat, difficulty swallowing and cough, wherein the amount of the botulinum toxin is ingested each day for four days.

8. The method of claim 7, wherein the botulinum toxin is selected from the group consisting of botulinum toxin types A, B, $C_1$, D, E, F and G.

9. A method for treating a symptom of gastroesophageal reflux disease that cannot be treated by an antacid, the method comprising the step of oral ingestion of a therapeutically effective amount of a botulinum toxin by a patient with a gastroesophageal reflux disease, thereby reducing the symptom of the gastroesophageal reflux disease that cannot be treated by the antacid.

10. The method of claim 9, wherein the botulinum toxin is selected from the group consisting of botulinum toxin types A, B, $C_1$, D, E, F and G.

11. A method for treating a symptom of gastroesophageal reflux disease that cannot be treated by a histamine H2 receptor blocker, the method comprising the step of oral ingestion of a therapeutically effective amount of a botulinum toxin by a patient with gastroesophageal reflux disease, thereby reducing the symptom of the gastroesophageal reflux disease that cannot be treated by the histamine H2 receptor blocker.

12. The method of claim 11, wherein the botulinum toxin is selected from the group consisting of botulinum toxin types A, B, $C_1$, D, E, F and G.

* * * * *